US010709751B2

(12) United States Patent
Ianiro et al.

(10) Patent No.: US 10,709,751 B2
(45) Date of Patent: Jul. 14, 2020

(54) CHARDONNAY GRAPE SEED EXTRACT

(71) Applicant: SHAKLEE CORPORATION, Pleasanton, CA (US)

(72) Inventors: Teodoro T. Ianiro, Concord, CA (US); Laurel A. Fisher, Los Angeles, CA (US)

(73) Assignee: SHAKLEE CORPORATION, Pleasanton, CA (US)

( * ) Notice: Subject to any disclaimer, the term of this patent is extended or adjusted under 35 U.S.C. 154(b) by 0 days.

(21) Appl. No.: 16/022,422

(22) Filed: Jun. 28, 2018

(65) Prior Publication Data

US 2018/0303895 A1 Oct. 25, 2018

Related U.S. Application Data

(62) Division of application No. 15/312,568, filed as application No. PCT/US2015/033234 on May 29, 2015, now Pat. No. 10,034,910.

(60) Provisional application No. 62/005,708, filed on May 30, 2014.

(51) Int. Cl.
| | |
|---|---|
| A61K 36/87 | (2006.01) |
| A23L 2/52 | (2006.01) |
| A23L 5/20 | (2016.01) |
| A23L 2/39 | (2006.01) |
| A23L 33/15 | (2016.01) |
| A23L 27/10 | (2016.01) |
| A23L 33/105 | (2016.01) |
| A23L 2/04 | (2006.01) |
| A23L 2/74 | (2006.01) |
| A23L 33/10 | (2016.01) |
| A23L 2/56 | (2006.01) |

(52) U.S. Cl.
CPC .............. *A61K 36/87* (2013.01); *A23L 2/04* (2013.01); *A23L 2/39* (2013.01); *A23L 2/52* (2013.01); *A23L 2/56* (2013.01); *A23L 2/74* (2013.01); *A23L 5/25* (2016.08); *A23L 27/10* (2016.08); *A23L 33/10* (2016.08); *A23L 33/105* (2016.08); *A23L 33/15* (2016.08); *A23V 2002/00* (2013.01); *A61K 2236/331* (2013.01); *A61K 2236/37* (2013.01); *A61K 2236/50* (2013.01); *A61K 2236/51* (2013.01)

(58) Field of Classification Search
None
See application file for complete search history.

(56) References Cited

U.S. PATENT DOCUMENTS

| | | | |
|---|---|---|---|
| 5,484,594 | A | 1/1996 | Frangi et al. |
| 5,912,363 | A | 6/1999 | Nafisi-Movaghar et al. |
| 6,214,382 | B1 | 4/2001 | Eguchi et al. |
| 6,544,581 | B1 | 4/2003 | Shrikhande et al. |
| 6,706,756 | B1 | 3/2004 | Fitzpatrick |
| 7,651,707 | B2 | 1/2010 | Kappagoda |
| 7,767,235 | B2 | 8/2010 | Shrikhande et al. |
| 7,959,963 | B2 | 6/2011 | Ying et al. |
| 8,075,929 | B2 | 12/2011 | Shrikhande et al. |
| 2004/0247714 | A1 | 12/2004 | Roe et al. |
| 2005/0129790 | A1 | 6/2005 | Folts et al. |
| 2009/0011056 | A1 | 1/2009 | Cheng et al. |
| 2011/0263698 | A1 | 10/2011 | Nagamine |
| 2012/0121742 | A1 | 5/2012 | Mairel |

FOREIGN PATENT DOCUMENTS

| | | |
|---|---|---|
| CN | 101100464 A | 1/2008 |
| CN | 102168120 A | 8/2011 |
| JP | 09-051791 | 2/1997 |
| JP | 2003-210110 A | 7/2003 |
| JP | 2009-189356 A | 8/2009 |
| WO | WO 2007/038685 A2 | 4/2007 |
| WO | WO 2009/012070 A1 | 1/2009 |
| WO | WO 2013/100003 A1 | 7/2013 |
| WO | WO 2013/165921 | 11/2013 |

OTHER PUBLICATIONS

Mironeasa et al. (2010) J. Agroalimentary Processes and Technologies 16(1): 1-6. (Year: 2010).*
Ma et al. (2017) Antioxidants 6, 71 (11 pages) (Year: 2017).*
Yilmaz et al. (2006) J. Food Composition and Analysis 19: 41-48. (Year: 2006).*
Sun et al. "Separation of Grape and Wine Proanthocyanidins According to Their Degree of Polymerization," *J. Agric. Food Chem.* 46(4):1390-1396 (1998).
Peng et al. "Quantitative Analysis of Polymeric Procyanidins (Tannins) from Grape (*Vitis vinifera*) Seeds by Reverse Phase High-Performance Liquid Chromatography," *J. Agric. Food Chem.* 49(1):26-31 (2001).

(Continued)

*Primary Examiner* — Terry A McKelvey
*Assistant Examiner* — Russell G Fiebig
(74) *Attorney, Agent, or Firm* — Klarquist Sparkman, LLP

(57) ABSTRACT

A novel grape seed extract is enriched in procyanidins, has total polyphenols of less than 70%, and has a low degree of polymerization (dp). Other fractions of the extract have minimal polyphenols, fiber, and protein, but contain more than 90% sugars. In some specific examples, the individual extracts are obtained by sequential ultrafiltration of a water extract of the grape seeds. A first ultrafiltration provides a first permeate (Fraction A) enriched in sugars which is useful as a flavorant, and a first retentate. The first retentate is reconstituted and subjected to a second ultrafiltration at a higher molecular weight cutoff to produce a second permeate (Fraction B) that is enriched in low molecular weight polyphenols, and a second retentate (Fraction C) that is enriched in seed fiber. The Fractions are individually suitable for different nutraceutical products, or can be combined with each other in any combination and/or with other nutraceutical agents to enhance vascular and cognitive health.

18 Claims, 1 Drawing Sheet

(56) References Cited

OTHER PUBLICATIONS

Saucier et al. "Rapid Fractionation of Grape Seed Proanthocyanidins," *J. Agric. Food Chem.* 49(12):5731-5735 (2001).
The Grape Seed Method Evaluation Committee "Grape Seed Extract," *Dry Creek Nutrition* pp. 1-17 (2001).
Cerpa-Calderon and Kennedy "Berry Integrity and Extraction of Skin and Seed Proanthocyanidins during Red Wine Fermentation," *J. Agric. Food Chem.* 56(19):9006-9014 (2008).
Liu et al. "Changes of Flavan-3-ols with Different Degree of Polymerization in Seeds of 'Shiraz', 'Cabernet Sauvignon' and 'Marselan' Grapes after Veraison," *Molecules* 15:7763-7774 (2010).
Catalano "Extraction, Purification and Characterization of Polyphenols from Uva di Troia ad Acino Piccolo Seeds and Skins for the Development of New Nutritional Supplements," *Universita degli Studi di Milano* pp. 2-162 (2012).
Liu et al. "Extraction and Characterization of Proanthocyanidins from Grape Seeds," *The Open Food Science Journal* 6:5-11 (2012).
Lorrain et al. "Evolution of Analysis of Polyhenols from Grapes, Wines, and Extracts," 18:1076-1100 (2013).
Ky et al. "Wine by-Products: Phenolic Characterization and Anti-oxidant Activity Evaluation of Grapes and Grape Pomaces from Six Different French Grape Varieties," *Molecules* 19:482-506 (2014).

\* cited by examiner

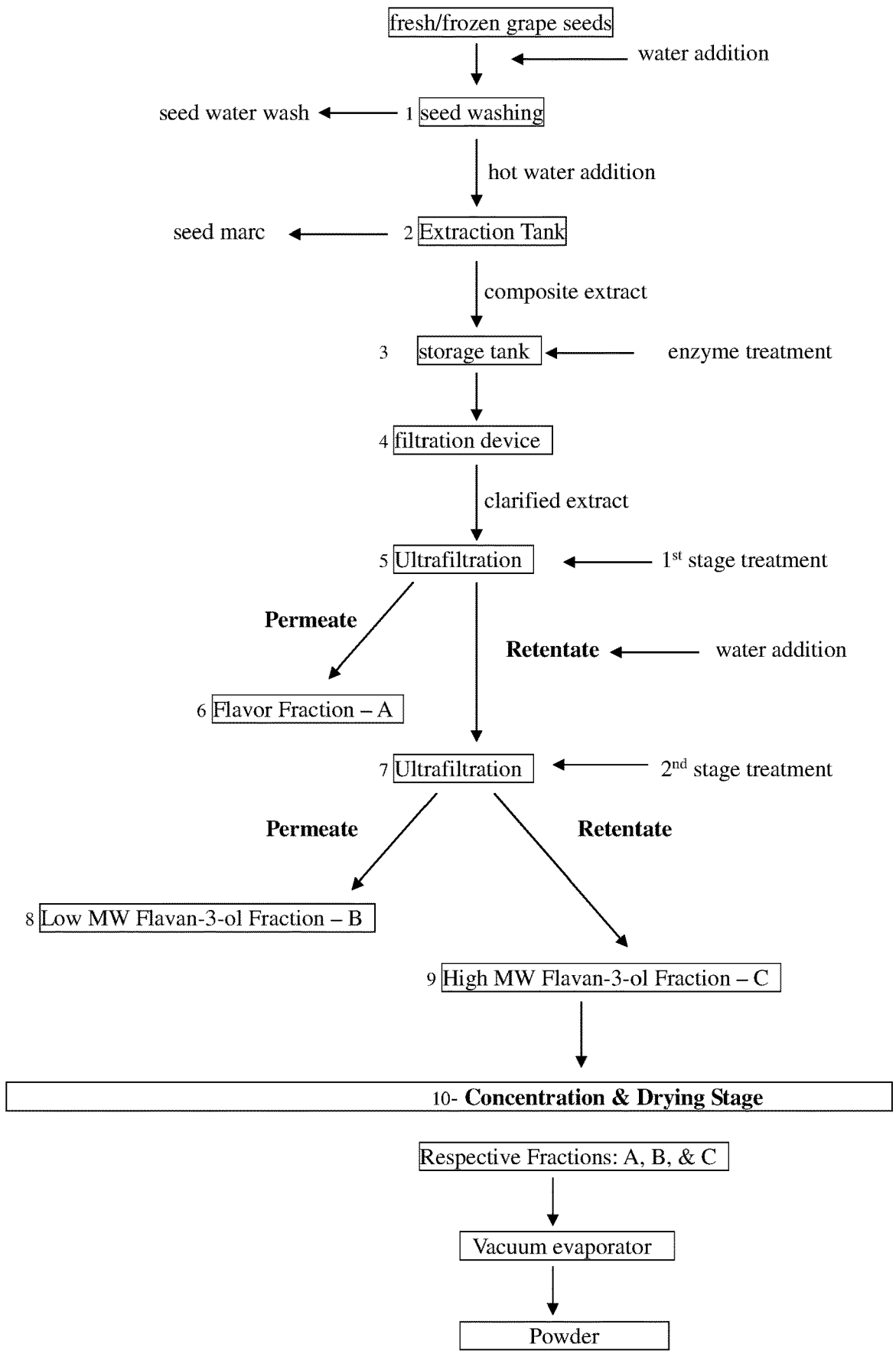

CHARDONNAY GRAPE SEED EXTRACT

CROSS REFERENCE TO RELATED APPLICATION

This is a divisional of U.S. patent application Ser. No. 15/312,568, filed Nov. 18, 2016, which is the U.S. National Stage of International Patent Application No. PCT/US2015/033234, filed May 29, 2015, published in English under PCT Article 21(2), which claims priority to U.S. Provisional Patent Application No. 62/005,708, filed on May 30, 2014. The above-listed applications are herein incorporated by reference in their entirety.

FIELD

This disclosure relates to grape seed extracts, grape seed extraction processes, and methods of obtaining fractions of the extract for making products beneficial to health.

BACKGROUND

Consumption of fruits and vegetables reduces the risk of several chronic diseases, most notably cardiovascular disease and cancer (Fung et al., Am J Clin Nutr 92:1429-1435, 2010). Although fruits and vegetables are important sources of vitamins and minerals, the salutary effects of these foods are attributed primarily to their content of fiber and antioxidants. Selected vitamins, such as vitamins C and E, exert antioxidant activity primarily through direct scavenging of oxygen and nitrogen radicals. Diverse phenolic substances (also called polyphenols) in fruits and vegetables also possess considerable antioxidant capacity and influence multiple cellular signaling cascades. Polyphenols are considered of key importance for mediating the health benefits of the Mediterranean diet and red wine (Del Rio et al., Antioxid Redox Signal 18:1818-1892, 2013).

Grapes are a particularly rich source of polyphenols, which is thought to explain the health benefits of consuming grapes, grape juice and wine. The predominant polyphenol species found in grapes (white grapes in particular) are similar to those identified in green tea and cocoa, namely flavanols or flavan-3-ols (Del Rio et al., Antioxid Redox Signal 18:1818-1892, 2013). Grape seeds are often considered a waste stream produced by the commercial production of grape juices, jellies, purees, and wine. The recognition that the seeds are the most concentrated source of polyphenols within the grape has prompted the development of a variety of industrial processes for grape seed processing to produce concentrated polyphenol extracts. Typically, these processes yield extracts containing the entire complement of phenolics found within the seed ranging from monomeric flavanols such as catechin and epicatechin to oligomers of two to ten of these monomeric units (known as procyanidins, proanthocyanidins, or oligomeric proanthocyanidins which are abbreviated as OPCs) to high molecular weight polymers of these monomeric units (known as polymeric procyanidins, tannins or condensed tannins). However, research over the last decade has revealed differing bioavailability and diverse biological actions of monomeric versus oligomeric versus polymeric catechin-based polyphenols. Unfortunately, most existing extraction processes for concentrating polyphenols employ harsh solvents that must be removed through complex fractionation schemes. Other fractionation methods use adsorption methodology that uses solvents such as ethanol for elution, necessitating specialized production facilities.

U.S. Pat. Nos. 3,435,407 and 4,698,360 disclose a method for the extraction of proanthocyanidins from pine bark, while minimizing the extraction of accompanying polymeric polyphenols (condensed tannins) using sodium chloride extraction and precipitation. These methods require repeated extraction with ethyl acetate. The ethyl acetate is then removed by evaporation, and oligomeric procyanidins are precipitated by the addition of chloroform.

U.S. Pat. No. 5,484,594 discloses a multistage process for preparing grape seed extract rich in oligomeric proanthocyanidins but that is almost free of monomers, which according to that patent are undesirable waste. The seeds are extracted with 80% aqueous acetone, filtered to remove polymeric waste product, then the solvent is evaporated, and the remaining polyphenols are concentrated. These steps are followed by further filtration to eliminate undesired monomers. The process uses chlorinated hydrocarbons, which are known carcinogens. The use of acetone and chlorinated hydrocarbons also increases the possibility of reactions with the procyandins and an alteration in the nature of the extracted procyanidins.

U.S. Pat. No. 5,912,363 discloses extraction of proanthocyanidins from plant material by heating an aqueous solid plant material mixture at temperatures of up to 350° F. under increased pressure and/or reduced oxygen, followed by membrane filtration to produce a permeate containing extracted proanthocyanidins. The extracted proanthocyanidins are then separated from the permeate by contacting the permeate with an adsorbent resin and subsequent elution with ethanol. All the examples are carried out at a temperature of 240° F., which is over the boiling point of water at atmospheric pressure. No selectivity for oligomers with low degrees of polymerization (dp) is disclosed.

U.S. Pat. No. 6,544,581 discloses a process for non-selectively extracting oligomeric and polymeric polyphenols from whole grapes, seeds or pomace using hot water extraction and a dual pH treatment. Oligomeric procyanidins having a dp up to 7 and polymeric procyanidins having a dp up to 16 are obtained in a process that uses mineral acids, such as sulfuric acid, then neutralized with an alkali metal base such as sodium or potassium hydroxide. The extract is treated with an adsorption resin and the polyphenols are eluted with ethanol. The resulting product has a very high level of total phenols, but relatively low percentages of monomeric procyanidins.

U.S. Pat. No. 7,767,235 produces a grape, grape seed or grape pomace extract by acidifying the extract with a mineral acid, such as sulfuric acid and then filtering it with diatomaceous earth. The extract is said to have about 5-15% monomeric procyanidins.

U.S. Pat. No. 8,075,929 produces a grape extract having about 5-15% monomers by extracting grapes at elevated temperatures, treating the extract with tannase, and acidifying the extract to a pH of about 1.5-2.5.

Prior procyanidin extraction processes generally extract grape seeds with biologically less desirable acidified organic solvents such as methanol, ethanol or acetone that must be removed prior to administration to a subject. Other prior extraction processes require high temperature processing. Some methods use pressurized liquid extraction (PLE) under high pressure and temperatures, successive chloroform in methanol extractions, or acidification with mineral acids such as sulfuric acids. Even with such potentially toxic treatments, the resulting extracts are not very enriched in monomeric procyanidins and have no more than about 15-17% monomers in the extract.

It would be desirable to provide a more biologically compatible process that is capable of extracting vegetable material, such as grape seeds, to obtain an isolated procyanidin extract having a low mean degree of polymerization (mdp). It would also be advantageous to provide such a method in which other biologically useful components of the grape seed were obtained and isolated, along with monomeric and dimeric flavanols.

SUMMARY

Although grape seeds are used for commercial production of polyphenol extracts and grape seed oil, grape seeds have been considered a relatively poor source of monomeric flavanols that are particularly beneficial to the health of vascular endothelium. Grape seeds have also been found to contain other beneficial dietary components, most notably fiber. On a dry weight basis, grape seeds can contain from 20-50% fiber whereas most commercial grape seed extracts are standardized to provide between 70-95% polyphenolics. Processes that produce these polyphenol-enriched extracts have removed valuable dietary fiber that can improve lipid profiles and enhance prebiotic functions. In addition, different components of grape seeds provide different specific health benefits. The methods disclosed herein permit the selective separation and retention of different fractions of grape seed extracts using a process that avoids the biological hazards of many of the prior processes. The separated fractions can be used separately or combined in any combination or proportion to prepare compositions having desired biological effects for an individual or group of individuals.

The disclosed extraction processes also overcome limitations of existing methods by using standard commercial processes and only a liquid water solvent (such as a pure water solvent) without the need for mineral acids to carry out the extraction. Extractions can also be performed below the boiling point of water (212° F.), and at atmospheric pressure. The beneficial components of the grape seeds are separated by sequential ultrafiltration steps into three fractions that are especially suited for different purposes: (A) a fraction containing mainly simple sugars and aromatic phenols for sweetening/flavoring purposes; (B) a fraction containing mainly low molecular weight flavanols, namely the monomeric and dimeric species that are useful for enhancing circulation; and (C) a fraction enriched in fiber and flavanol oligomers and polymers for imparting prebiotic effects. It is also notable that the latter two fractions (B and C) contain less than 1% lipid content as opposed to currently available commercial grape seed extracts that contain 2-3% lipid content. Typically, higher lipid content imparts a waxy, sticky characteristic that resists compression and impedes formulation of grape seed extract into tablets. Grape seed extracts with 2-3% lipid content tend to cause tablets to develop streaking and capping and also are more incompatible with manufacturing machinery due to stickiness. Thus, grape seed extract formulations are most commonly found in capsules or in more expensive forms such as soft gels. The extremely low lipid content of the polyphenol enriched fractions described below enables their formulation into tablets.

Although the disclosed process can be used to extract and separate different components of many seeds, and many grape seeds, Chardonnay grape seeds in particular are well suited for the disclosed extraction process. Chardonnay varietal is one of the most popular wines worldwide and thus abundant quantities of grape seed are generated. Moreover, Chardonnay seeds are reported to contain a relatively high content of epicatechin (Fuleki and Ricardo da Silva, J Agric Food Chem 45:1156-1160, 1997; Yilmaz and Toledo, J Agric Food Chem 52:255-260, 2004), a flavanol monomer that is reported to mediate beneficial actions on human endothelial function and may underlie, at least in part, the effects of cocoa and grape seed extract on circulatory function (Jimenez et al., J Agric Food Chem 60:8823-8830, 2012).

In a particular example of the method, washed grape seeds are extracted with hot water at a temperature of about 100-200° F., for example 120-195° F., such as 130-190° F. The initial extract is enzymatically treated and fine-filtered to substantially remove insoluble plant material and produce a clarified extract. The clarified extract is processed by a first ultrafiltration to obtain a first permeate and a first retentate, wherein larger molecular weight polymers are removed from the first permeate, and the first permeate comprises at least 80% sugars. The first retentate is reconstituted then processed by a second ultrafiltration to obtain a second permeate that contains polyphenols having an mdp of less than 3, for example less than 2.5, and a second retentate enriched in fiber and polyphenols, wherein the polyphenols have an mdp of greater than 5. In particular examples, the first ultrafiltration is performed with an ultrafiltration membrane having a molecular weight cutoff in the range of 1-5 kD, and the second ultrafiltration is performed with a membrane having a molecular weight cutoff in the range of 100-500 kD.

Also disclosed herein are compositions that comprise an isolated or purified Chardonnay seed extract wherein the flavanols of the extract have a mean degree of polymerization of less than 3, for example less than 2.5, and a total polyphenol content of less than 70%, and in some examples the polyphenol content is less than 50%. In some examples, the flavanols in the Chardonnay seed extract are more than 50% monomeric flavanols, and/or contain less than 1% lipids. In particular examples, the Chardonnay seed extract contains 38-50% polyphenols, 9-12% fiber, 1-2% protein, 25-30% sugars and less than 1% lipid.

Another disclosed composition comprises an isolated or purified Chardonnay seed extract wherein the composition contains 45-55% polyphenols, 26-30% fiber, and less than 1% lipid. In some examples, the Chardonnay seed extract further contains 2-3% protein and less than 1% sugars.

Another disclosed composition comprises an isolated or purified Chardonnay seed extract wherein the composition contains 90-95% sugars, less than 1% polyphenols, less than 1% protein, and less than 3% lipid.

In other embodiments, the composition is a combination of two or three of the separate compositions.

Another disclosed embodiment is an isolated or purified water extract of Chardonnay seed, wherein the extract is one of Fraction A, B or C:

|  | Fraction A | Fraction B | Fraction C |
| --- | --- | --- | --- |
| Polyphenols (GAE) | <1 | 38-50 | 45-55 |
| Fiber | <1 | 9-12 | 26-30 |
| Protein | <1 | 1-2 | 2-3 |
| Lipid | <3 | <1 | <1 |
| Sugars | 90-95 | 25-30 | <1 |

In some embodiments, a composition contains only Fraction A or Fraction B or Fraction C. In other examples, a composition contains combinations of the previously separate Fractions, such as a combination of Fractions A and B, A and C, B and C, or A, B and C.

In yet another example, the Chardonnay seed extract is an extract obtained by extracting the Chardonnay seeds only with water, for example by water solvent extraction without the use of alcohol solvents (such as methanol or ethanol solvents), mineral acid solvents (such as sulfuric acid), or resins. The water extract may be further subjected to ultrafiltration which produces an extract having a lipid content of less than 1%. In some examples, the water extract having a lipid content of less than 1% further contains flavanols having a mean degree of polymerization of less than 3, and in some examples less than 2.5. In some examples these extracts contain 38-50% polyphenols, and in some examples these extracts contain 45-55% polyphenols.

The extract, in liquid or dry form, may be formulated into a nutritional composition, for example by combining it with nutraceutical carriers, for example non-naturally occurring nutraceutical carriers, for example by incorporation into a dosage form such as a tablet or capsule or prepared food product that is not found in nature (such as an energy bar).

The isolated extracts and compositions that contain the extracts can be used to support, maintain or improve cardiovascular or cognitive health by administering them to a subject. The extract, in liquid or dry form, is suitable for administration to a subject, either alone or in combination with other nutrients such as one or more of guarana extract, vitamin B6, vitamin B12, folate, blueberry powder/extract and green coffee bean extract. In particular examples, the low mdp fraction obtained with the second permeate is administered, alone or in combination with one or more of the other nutrients. In some examples these compositions are used to improve circulatory and cognitive health.

The foregoing and other objects, features, and advantages of the invention will become more apparent from the following detailed description, which proceeds with reference to the accompanying figures. Nothing in this Summary of the Disclosure shall be construed to imply the criticality of any aspect of the methods and compositions summarized herein.

BRIEF DESCRIPTION OF THE DRAWINGS

FIG. 1 is a schematic illustration of an embodiment of the extraction method.

DETAILED DESCRIPTION

I. Terms

The following explanations of terms and methods are provided to better describe the present disclosure and to guide those of ordinary skill in the art in the practice of the present disclosure. As used herein and in the appended claims, the singular forms "a" or "an" or "the" include plural references unless the context clearly dictates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. It is further to be understood that any quantitative values are approximate whether the word "about" or "approximately" or the like are stated or not. All percentages and ratios are calculated by weight unless otherwise indicated.

Administration: To provide or give a subject an agent, such as a composition that includes a chardonnay seed extract, by any effective route. Exemplary routes of administration include, but are not limited to, oral, injection (such as subcutaneous, intramuscular, intradermal, intraperitoneal, intravenous, and intratumoral), sublingual, transdermal, intranasal, topical and inhalation routes.

Blueberry powder or extract: Blueberries, such as organic blueberries, are dried through typical commercial means such as drum-drying, microwave-drying or freeze-drying and then milled into powders. "Blueberry extract" refers to solvent extracted blueberries, for example extracts obtained through typical water or water/ethanol liquid extractions to yield extracts.

Chardonnay grape: A green-skinned grape variety used to make white wine, it is also known as *Vitis vinifera* Chardonnay.

Degree of Polymerization: The degree of polymerization (dp) is the number of monomeric units in a polymer or oligomeric molecule. The mean degree of polymerization (mdp) is defined as the mean or average molecular length (number of monomeric units that form the molecule) of constituent flavanols in a complex mixture (such as an extract) of flavanol species that includes monomers, oligomers and polymers. The lower the mdp, the higher the percentage of monomers and dimers in the mixture. The mdp can be expressed as the number of monomeric flavanol units in an average polymer chain in a sample that is measured. The average length of constituent molecules in a complex mixture can be determined, for example, using methods such as thiolysis, wherein acid catalyzed cleavage of the oligomers followed by benzylthioether derivatization is performed prior to quantitation of the derivatized monomers by mass spectroscopy (Gu et al., J Agric Food Chem 50:4852-4860, 2002) and gel permeation chromatography wherein oligomers having dps of 1 to 10 are separated chromatographically by molecular size and quantitated with mass spectrometry (Hammerstone et al., J Agric Food Chem 47:490-496, 1999).

Effective Amount: An amount of a composition that alone, or together with an additional agent(s) (for example additional antioxidants), induces the desired response. The preparations disclosed herein can be administered in therapeutically (for example nutraceutically) effective amounts. The effective amount can be administered in a single dose, or in several doses, for example daily. However, the effective amount can depend on the subject being treated, the severity and type of the condition being treated, and the manner of administration.

Excipient: An inactive substance used as a carrier for the active ingredients of a composition. Excipients can include substances that are used to bulk up formulations with very potent active ingredients, allow for convenient and accurate dosage, stabilize the active ingredients, and make the delivery system optically and/or organoleptically acceptable. Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like.

Extract: A solution or other preparation of at least some of the active ingredients of a plant or one or more of its parts, such as its fruit or seeds. The extracts disclosed herein are solvent extracts, in which seeds are exposed to a liquid extract solvent (such as heated water) to remove active principles from the seeds. An extract initially obtained by solvent extraction may be converted into a dried form and still be considered an "extract." An "aqueous" or "water" extract refers to an extract obtained by solvent extraction with water and no other solvent (such as ethanol).

Flavonoids: A class of plant secondary metabolites, on a dry weight basis, grape seeds contain about 4-8% flavonoids. Flavonoids constitute an important group of dietary polyphenolic compounds that are widely distributed in plants. More than 4000 chemically unique flavonoids have been identified in plant sources, such as fruits, vegetables, legumes, nuts, seeds, herbs, spices, flowers, as well as in beverages such as tea, cocoa, beer, wine, and grape juice.

Flavonoids in grape seeds refer primarily to flavan-3-ols, specifically (+)-catechin, (−)-epicatechin, and (−)-epicatechin 3-gallate, and complexes thereof. The flavan-3-ols in grape seeds are present in monomeric, oligomeric or polymeric forms. Two or more chemically linked flavan-3-ol monomers are called proanthocyanidins or oligomeric proanthocyanidins ("OPCs"), which includes procyanidins and prodelphinidins. OPCs containing two monomers are called dimers, three monomers are called trimers, four monomers are called tetramers, five monomers are called pentamers, etc. The oligomers have chain lengths of 2 to 10; polymers represent components with chain lengths greater than 10. Thus, oligomers in grape extracts include, for instance, dimers and trimers, and there is evidence that the polymers can have as many as 50-100 units.

In order for polyphenolic compounds to be used commercially as a grape extract, these compounds have to be separated from grapes in a more concentrated form. Scientific studies have shown that the antioxidant power of proanthocyanidins is 20 times greater than vitamin E and 50 times greater than vitamin C. Extensive research suggests that grape seed extract is beneficial in many areas of health because of its antioxidant effect to bond with collagen, promoting youthful skin, cell health, elasticity, and flexibility. Other studies have shown that proanthocyanidins help to protect the body from sun damage, to improve vision, to improve flexibility in joints, arteries, and body tissues such as the heart, and to improve blood circulation by strengthening capillaries, arteries, and veins.

Folate: Also known as Vitamin B9, folate is a water soluble vitamin of the B complex. Folate is the naturally occurring form in food, and folic acid is a synthetic form often found in dietary supplements and vitamin-fortified foods. The terms "folate" and "folic acid" are often used interchangeably, and will be so used in this specification, such that reference to "folate" includes folate as well as folic acid and other forms of nutritionally acceptable folate, such as non-naturally occurring folate, that are not present in food. Hence "folate" will include other forms or biological precursors or biologically activated forms, such as methylfolate, 5-methyltetrahydrofolate (5-MTHF), and optically racemic or pure forms of folate, such as L-5-MTHF. Methylfolate is a form of the vitamin that is sometimes included in supplements, particularly for individuals who have MTHFR polymorphisms that are associated with lower levels of MTHFR enzyme activity. Folate is effective to reduce serum levels of homocysteine, thereby reducing the risk of cardiovascular disease and dementia in some subjects.

Green coffee bean extract: An extract (for example a liquid extract) of green coffee beans. Green coffee bean extract is typically a hot water or ethanol/water extract of dried green unroasted coffee beans (*Coffea Arabica*) containing standardized amounts of chlorogenic acids and caffeine.

Guarana extract: Typically a water/ethanol extract of the seeds of a South American plant, guarana (*Paullinia cupana*), usually standardized to 4-10% alkaloids (caffeine plus theobromine) and also containing 5-15% polyphenols.

HPMC or hydroxypropyl methyl cellulose: A semisynthetic, inert, viscoelastic polymer used as a lubricant or excipient having the general structure shown below:

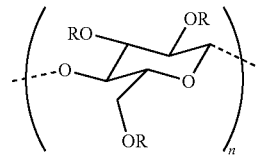

$R = H$ or $CH_3$ or $CH_2CH(OH)CH_3$

Nutrients: Nutrients are nutritious components in foods that an organism uses to survive and/or thrive. Although nutrients are present in food, a nutrient as used herein can be either naturally occurring or synthetically manufactured. A "whole food nutrient" refers to a nutrient that is found in whole food and not synthetically made.

Pharmaceutically Acceptable Vehicles: The pharmaceutically acceptable vehicles (carriers) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more compositions, such as one or more grape seed extract compositions, and additional naturally or non-naturally occurring pharmaceutical agents that would not be found with the grape seed extracts in nature. The use of pharmaceutically acceptable carriers does not imply that that product so made is useful only for pharmaceutical purposes. Rather it implies that the product is suitable for administration to or consumption by a subject, for example as a pharmaceutical or nutriceutical that is suitable for oral ingestion by a subject.

In general, the nature of the vehicle will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid vehicles can include, for example, pharmaceutical grades of mannitol, lactose, starch, or magnesium stearate. In addition to biologically-neutral vehicles, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polyphenols: Polyphenols from grapes and cocoa have been found to enhance both cardiovascular function and cognitive health. Flavanols (also called flavan-3-ols) represent the majority of grape seed and cocoa polyphenols; this class of phenolic compounds ranges from monomeric species such as catechin and epicatechin to oligomers (often termed proanthocyanidins) to polymers (often termed tannins or condensed tannins). The term "phenolic" is used interchangeably with the term polyphenol in the art and in this specification.

Grape seeds are waste products of the winery and grape juice industry. These seeds contain lipid, protein, carbohydrates, and 4-8% polyphenols (dry weight) depending on the variety. Grape seed extract is therefore a powerful antioxidant that protects the body from premature aging, disease, and degeneration.

Prebiotic: Non-digestible food ingredients that stimulate the growth and/or activity of beneficial bacteria in the digestive system.

Purified: The term purified does not require absolute purity; rather, it is intended as a relative term. Thus, for example, a purified substance is one in which the substance is more enriched than the substance in its natural environment, for example in a fruit (e.g., grape). In one embodiment, a preparation is purified such that the substance represents at least about 5% (such as, but not limited to, at least 10%, 20%, 30%, 40%, 50%, 70%, 80%, 90%, 95%, 98% or 99%) of the total content of the preparation. In an example, a disclosed composition with antioxidant activity includes a chardonnay grape seed extract with a minimum of purity of at least 50%, 70%, 80%, 90%, 95%, 98% or 99% (by weight).

Range: With respect to ranges, the term "in the range of x to y" or "from x to y" includes any value between x and y, as well as the endpoints x and y.

Selective extraction: Selective extraction refers to preferential extraction of a target (such as monomeric procyanidins). In some embodiments, selective extraction means that the target is the predominant species extracted.

Ultrafiltration: A type of membrane filtration in which forces (such as pressure or concentration gradients) lead to a separation through a semipermeable membrane. Ultrafiltration membranes are typically characterized by the molecular weight cut off (MWCO) of the membrane. Suspended solids and solutes of higher molecular weight are retained in the retentate, while water and lower molecular weight solutes pass through the membrane in the permeate. Different types of modules can be used for ultrafiltration processes. Examples of such modules are tubular elements that use polymeric membranes cast on the inside of plastic or paper tubes; hollow fiber designs that contain multiple hollow fibers; spiral wound modules in which flat membrane sheets are separated by a thin meshed spacer material that is rolled around a central perforated tube and fitted into a tubular steel pressure vessel casing; and plate and frame assemblies that use a membrane placed on a flat plate separated by a mesh like material through which the filtrate passes.

Unit dose: A physically discrete unit containing a predetermined quantity of an active material calculated to individually or collectively produce a desired effect, such as a therapeutic effect. A single unit dose or a plurality of unit doses can be used to provide the desired effect or activity, such as antioxidant activity. In one example, a unit dose includes a desired amount of an agent that promotes cardiovascular or cognitive health. In another example, the unit dosage form contains multiple predetermined dosages of the active material.

Vitamin B6: A water-soluble vitamin that is part of the B vitamin complex. "Vitamin B 6" includes all nutritionally acceptable forms of this vitamin, such as pyridoxine, pyridoxine 5'-phosphate, pyridoxal, pyridoxal 5'-phosphate, pyridoxamine 5'-phosphate, and 4-pyridoxic acid. It is sometimes provided in dietary supplements as the pyridoxine hydrochloride form or the active pyridoxal phosphate form. Vitamin B6 is an active cofactor in many reactions of amino acid metabolism.

Vitamin B12: Another water-soluble vitamin of the B vitamin complex. It is known as cobalamin, and is provided in several different forms, such as non-naturally occurring forms, in dietary supplements. "Vitamin B12" refers to all forms of cobalamin, such as cyanocobalamin, hydroxocobalamin and methylcobalamin. Vitamin B12 has been found to be important to neuropreservation and cognitive enhancement. Deficiencies of it are associated with mild cognitive impairment and dementia. Vitamin B12 deficiency is believed to be widespread, especially in older populations, and it constitutes one of the primary forms of reversible dementia and neurological impairment. Vitamin B12 is also required for erythropoiesis (production of red blood cells) and the conversion of homocysteine to methionine. A deficiency of Vitamin B12 is especially problematic for individuals who have particular mutations in the MTHFR enzyme. Vitamin B12 is often provided in the form of cyanocobalamin, but methylcobalamin and 5-deoxyadenosylcobalamin are the forms of Vitamin B12 that are active in human metabolism. In particular examples herein, Vitamin B12 is provided as cyanocobalamin, but any nutritionally acceptable form of cobalamin is included in the term Vitamin B12.

II. Description of Several Embodiments

This detailed description sets forth several embodiments of a method for solvent extracting vegetable material, such as grape seed, for example Chardonnay seeds. The mere disclosure of a particular extraction detail is not intended to imply the criticality of any such detail, nor is the presentation of data obtained with particular embodiments of the method intended to imply that the method is limited to particular steps that were used to obtain such data.

The disclosed method permits the extraction of proanthocyanidins and other beneficial nutraceutical agents from plant material, for example from seeds, such as grape seeds, which in a particular example are Chardonnay seeds. Grape seeds are extracted with water at a temperature of about 100-200° F., for example 120-195° F., such as 130-190° F., then the extract is enzymatically treated and fine filtered to substantially remove insoluble plant material in the extract. The water extract is clarified prior to ultrafiltration by filtering with a filter that excludes material larger than 1-10μ, for example 1-5μ, in particular examples any solid plant material having a size greater than 1μ, 5μ, or 10μ. The fine filtered extract is then concentrated to a solids content of less than 10%, for example to a solids content of 5-10%, to reduce its volume while maintaining it sufficiently dilute to minimize clogging of ultrafiltration filters during the subsequent ultrafiltration step.

The enzymatically treated and fine filtered extract is then further processed by ultrafiltration to obtain a first permeate and a first retentate, wherein larger molecular weight polymers are removed from the first permeate, and the first permeate comprises at least 80% sugars. This first ultrafiltration step produces a sugar/aromatic phenolic fraction (A). The first retentate is reconstituted, then processed by ultrafiltration to obtain a second permeate (B) that contains polyphenols having a mean degree of polymerization (mdp) of less than 3 or 2.5 (for example 2-3 or 2-2.4), and a second retentate (C) enriched in fiber and polyphenols, wherein the polyphenols in the second retentate (C) have a mdp of greater than 5 (for example 5-6, for example 5.6). Any or all of the first and second permeates and second retentate may be concentrated and dried to provide a retained end product that is commonly saved in a powdered form.

In particular examples, the enzymatically treated fine filtered extract is first processed using an ultrafiltration membrane having a maximum molecular weight cutoff of 5 kD. For example, a range of maximum molecular weight cutoffs of the first ultrafiltration membrane is 1-5 kD. In some examples within this range, the minimum molecular range cutoff of the first ultrafiltration membrane is 1, 2, 3 or 4 kD. In other examples within this range, the maximum molecular weight cutoff of the first ultrafiltration membrane is 2, 3, 4 or 5 kD. Irrespective of the 1-5 kD range, in other examples the minimum molecular weight cutoff of the first ultrafiltration membrane can be 1, 2, 3 or 4 kD, and the maximum molecular weight cutoff can be 2, 3, 4 or 5 kD.

The first retentate is reconstituted in water and further processed using ultrafiltration with a membrane having a maximum molecular weight cutoff of 500 kD. For example, a range of maximum molecular weight cutoffs of the second ultrafiltration membrane is 100-500 kD. In some examples within this range, the minimum molecular weight cutoff of the second ultrafiltration membrane is 100, 200, 300 or 400 kD. In others examples within this range, the maximum molecular weight cutoff is 200, 300, 400 or 500 kD. Irrespective of the 100-500 kD range, in other examples the minimum molecular weight cutoff can be 100, 200, 300 or 400 kD, and the maximum molecular weight cutoff can be 200, 300, 400 or 500 kD.

The described process efficiently separates the grape seed extract into biologically compatible fractions having different biological uses. The first permeate (Fraction A), for example, may include greater than 80% sugars, less than 5% lipids, and less than 1-2% polyphenols, and be suitable as a flavoring material. The second permeate (Fraction B), for example, may include less than 1% lipids and at least 38% polyphenols, wherein less than 10% of the polyphenols contain more than 10 monomeric units. In some embodiments, the second permeate (Fraction B) contains less than 70% total polyphenols, for example less than 60% or less than 50% total polyphenols. In some examples, Fraction B contains between 38-50% phenolics. In this and other embodiments the polyphenols in the extract are at least 50%, 60%, or even 70% monomers, for example 50-80% monomers. Fraction B is particularly suited for absorption from the gastrointestinal tract to enhance vascular and therefore cognitive health. The second retentate (Fraction C), for example, may include 25-30% fiber, 45-55% polyphenols having an mdp of greater than 5, 2-3% proteins, and less than 1% lipid.

In some optional embodiments, hydroxypropyl methylcellulose (HPMC) is added to the extract prior to ultrafiltration to increase efficiency of ultrafiltration.

Compositions can be made that include any one, two or three of Fractions A, B and C. The composition can be formulated as a dietary supplement or functional food. Separate fractions are particularly suited for different organoleptic or nutritional purposes. For example, Fraction A, which contains mostly sugars (fructose and glucose) can be formulated or used as a natural flavorant. As another example, Fraction B which contains procyanidins having a low mdp can be formulated or used as a nutritional supplement to enhance vascular or cognitive health. As yet another example, Fraction C which is enriched in fiber and polyphenols having a higher mdp can be formulated or used as a prebiotic nutraceutical in tablet or powder form.

In yet other embodiments, the nutritional supplement that contains any combination or all of Fractions A, B and C can be combined with other nutrients, such as one or more or all of guarana extract, vitamin B6, vitamin B12, folate, blueberry powder or blueberry extract and green coffee bean extract. Such a composition is ideally suited as a supplement to support vascular and/or cognitive health. In particular embodiments, Fraction B can be combined with one or more of these other nutrients. In other particular examples, Fraction B can be combined with all of guarana extract, vitamin B6, vitamin B12, folate, blueberry powder or blueberry extract and green coffee bean extract.

In another example, the extraction method includes the steps of providing an aqueous mixture of solid plant material (such as grape seeds) which has been prepared by extracting grape seeds in heated water, such as water heated to over 100° F. but less than the boiling point of water (212° F.), for example in the range of 100-200° F., for example 120-195° F., such as 130-190° F. The extract is then enzymatically treated to reduce its content of cellulose, pectin and proteins. Enzymes are used, for example in the crude extract (first water extract) prior to fine filtration, to break down larger molecules in the plant material such as fiber, cellulose, pectin and/or protein. The breakdown of these molecules eases filtration with any type of micron scale filtering (fine filtering) and ultrafiltration. As such, proteases, pectinases, and cellulases can be used individually or in combination depending on what the content of the starting material contains and what is desired in the end product of the process. For example, if the starting material contains no protein then a protease would not be used. If pectin is the only large compound in the starting material and it is not desired in the final product, then only the liquid pectinase preparation, for example Rapidase® Adex-G (DSM, Centerchem, Inc.), might be applied at 0.01-0.1% (vol/vol) for 1-3 hours.

In examples of the process disclosed herein, it is desired to retain some fiber but not protein, hence enzymes and doses are chosen that do not destroy all of the fiber that is ultimately collected in Fraction C.

Although many different enzymes could be used for this purpose, a particularly disclosed non-limiting example is SCOTTZYME KS from Scott Laboratories (Petaluma, Calif.) which contains a blend of enzymes from *Aspergillus niger*. This blend of enzymes is suitable for use with juices to enhance settling and filtration and can be applied to the extract at 0.01-0.1% (vol/vol) for 8-16 hours. The enzymatically treated water extract is then subjected to fine filtration, with a 1-10μ filter, more preferably 1-5μ) and concentrated to no more than 10% solids. The concentrated extract is then subjected to ultrafiltration with an ultrafiltration membrane having a molecular weight cutoff in the range of 1-5 kD to produce a sugar-containing first permeate (Fraction A) and a first retentate (material that does not pass through the ultrafiltration). The first retentate is reconstituted in water to no more than 10% solids and subjected to a second ultrafiltration with an ultrafiltration membrane having a molecular weight cutoff of in the range of 100-500 kD. The resulting permeate (Fraction B) and retentate (Fraction C) are then collected and may be further processed, for example by drying to produce a powder.

In another example, HPMC is added to the initial unfiltered aqueous seed extract to reduce the tannin content of the initial liquid extract to increase the speed of ultrafiltration. When HPMC is used, fractions A and B are unchanged from the description of fractions A and B above, however Fraction C will contain more fiber (greater than 50%, for example 50-60%) and the polyphenolic species of Fraction C will comprise mainly smaller procyanidins with an mdp of 2.5-2.9. This modified Fraction C having higher fiber content would therefore be expected to have a greater beneficial effect on blood lipid profiles, in addition to its prebiotic activities.

Example 1

Extraction Method

A particular non-limiting embodiment of the extraction process is shown in FIG. 1. Chardonnay grape seeds 1 (fresh, frozen or dried) are washed at step (1) with potable room temperature water. Various weight ratios of water to grape seeds can be used, for example a ratio of 2:1 to 10:1, but the illustrated example uses a 5:1 ratio [weight:weight] of water to grape seeds which are washed with continuous mixing for 15 minutes. This process is repeated at least two times or more, preferably three times and up to four times. In some examples the water, for example the water of the first wash, is neutralized by addition of a base to reduce extraction of polyphenols into the wash while enhancing extraction of sugars into the wash. In a particular example, the water is neutralized by addition of sodium bicarbonate, such as 0.1% sodium bicarbonate, to the water. Each wash, containing mostly sugars, lipids, and some organic acids, is discarded.

The washed seeds are then transferred to an extraction tank at step 2 and are extracted twice in heated water (100-200° F. or 130-190° F.), for example at about 130° F. or 175° F. (5:1 ratio of water to seeds [weight:weight]) for 1-3 hours, for example for a period of 2.5 hours. The seed marc is discarded and the extracted liquids are combined and filtered to remove insoluble plant material (USMESH 270), then this composite extract is placed in a storage tank 3 where it is treated with enzyme to reduce the content of cellulose, pectin and proteins to facilitate subsequent filtration. A commercial example of such an enzyme is SCOT-TZYME KS (Scott Laboratories). Enzyme treatment is applied at 0.01-0.1% (vol/vol) and carried out for 12 to 24 hours, preferably for 16 hours at 45-100° F., preferably not more than 65° F. Optionally, after enzyme treatment, the process may include adding hydroxypropylmethylcellulose (HPMC; low viscosity, pharmaceutical grade) at 1 gram/liter and mixing for one hour at 60 to 80° F., preferably at 65° F. Following enzyme treatment (and optionally HPMC addition), the liquid extract is clarified using fine filtration (1-10μ filter, preferably 1-5μ) in a filtration/separator device 4 (for example a unit such as the Nozzle Separator HFC 15-01-177, GEA Wesphalia Group) and the clarified extract is concentrated to 5-10% solids, preferably <10% solids.

The concentrated extract is then subjected to ultrafiltration 5 (with standard nominal molecular weight cutoff ultrafiltration membranes of no greater than 5000 daltons (or 5 kD), such as a Polyethersulfone membrane system, for example the SUPER-COR UF system series (Koch Industries). The ultrafiltration step 5 yields a permeate 6, which is Fraction A, comprised of compounds having molecular weights of less than 5000 daltons (5 kD) and containing not less than 80% sugars (typical range 80-95%, such as 90-95%) comprised mainly of fructose and glucose, 9-10% water, less than 5% lipid, less than 5% minerals, and less than 1% phenolic compounds; the phenolic compounds include trace amounts of multiple aromatic/flavor molecules such as terpenes and vinylphenol compounds. Fraction A has applications for natural flavoring of edible nutritional supplements in the form of bars, gels, and "gummies" at standard doses of 5-20% of each composition.

The retentate (material that does not pass through the ultrafiltration membrane) remaining from the low molecular weight ultrafiltration is reconstituted in water to 5-10% solids concentration, preferably not more than 10% solids and subjected to a second ultrafiltration process 7 with a 100-500 kD cutoff (for example 100 kD cutoff) ultrafiltration membrane, such as a Polyethersulfone membrane system, for example the SUPER-COR UF system series (Koch Industries), although other membrane systems could be used. The resulting permeate 8, which is Fraction B, and retentate 9, which is Fraction C, are dried at step 10 by conventional methods such as lyophilization or radiant zone drying and milled to yield powders.

Fraction B powder is comprised mainly of polyphenols (at least or about 38% polyphenols), specifically, flavanols such as monomeric catechin and epicatechin and small oligomeric procyanidins (containing less than 10 units). Although molecules having a molecular weight of up to 500,000 daltons are able to permeate the ultrafiltration membrane, it was unexpectedly found that greater than 90% of the procyanidin species in Fraction B do not exceed polymers of 10 units and are comprised mainly of monomers, dimers and trimers yielding an mean degree of polymerization (mdp) value of 2 to 2.4. Fraction B also contains small amounts of fiber (9-12%), sugars (25-30%), protein (1-2%), lipid (<1%) and trace amounts of minerals such as calcium and magnesium. Wide-ranging applications exist for Fraction B based on the reported effects of monomeric and low molecular weight procyanidins on vascular health as well as the antioxidant capacity of flavanols. This fraction could be added to all forms of nutritional supplements designed to promote healthy circulation or provide antioxidant protection at doses of 50 mg to 2 grams per serving.

Fraction C powder (retentate of second ultrafiltration) is highly enriched with both fiber (26-30%) and polyphenols (45-55%). In contrast to Fraction B, however, the polyphenolic fraction is comprised primarily of high molecular weight procyanidins and tannins with an mdp value of greater than 5, for example 5-10, and particularly 5.6. Fraction C also contains small amounts of sugar (<1%), protein (2-3%), lipid (<1%) and minerals (trace amounts). Fraction C is suited ideally to serve as a prebiotic nutraceutical in tablet or powder form or for fortifying functional foods in doses ranging from 2-20 grams per serving.

The optional use of HPMC reduces the tannin content of the initial liquid extract, thereby facilitating speed of ultrafiltration. In this case, Fractions A and B remain essentially identical in composition as described above. However, Fraction C now is comprised of mainly fiber (50-60%) and the polyphenolic species are comprised of mainly smaller procyanidins with an mdp of 2.5-2.9. Usage in nutraceuticals and/or functional foods at 2-20 grams per serving would impart prebiotic activity; the increased fiber content would be expected to improve blood lipid profiles.

Fractions A, B and C are ideally suited to serve different nutraceutical functions when used separately. Nevertheless, certain applications can employ combinations of two or three of the fractions. For example, a functional food such as an energy or fiber bar might contain both Fraction C to provide fiber and Fraction A to provide flavoring.

Example 2

Analytical Results

Whole Chardonnay seeds (fresh grape seeds typically contain 40-50% water) and Fractions A, B and C (produced as described in Example 1 using ultrafiltration membranes having a maximum cut off 5 kD for the first and 500 kD for the second ultrafiltration membrane) were analyzed for nutritional content and for polyphenols (gallic acid equivalents [GAE]) by a modified method of Folin-Ciocalteu (Singleton and Rossi, Am J Enol Vitic 16:144-158, 1965). As shown in Table 1, Fraction A is almost completely sugar, 90% of which is fructose and glucose. Fraction B is comprised of mainly low molecular weight polyphenols such as monomeric and dimeric flavanols (see Tables 2 and 3 below) along with a small amount of fiber. Fraction C is comprised of flavanol oligomers and polymers (tannins) as described in Tables 2 and 3 below and is enriched in fiber content. Importantly, Fractions B and C contain extremely low levels of lipid (<1%) whereas the average lipid value of commercially available grape seed extracts shown in Table 3 was 2.3%. The low level of lipid in Fractions B and C allows for tablet formulations unlike the other commercial extracts which require delivery in capsule (bulky, difficult to swallow) or soft gel forms (expensive to manufacture).

TABLE 1

Nutritional constituents of Chardonnay gape seeds and Extract Fractions A, B, and C (% dry basis)

|  | Whole seed | Fraction A | Fraction B | Fraction C |
|---|---|---|---|---|
| Polyphenols (GAE) | 4-10 | <1 | 38-50 | 45-55 |
| Fiber | 30-45 | <1 | 9-12 | 26-30 |
| Protein | 10-20 | <1 | 1-2 | 2-3 |
| Lipid | 9-15 | <3 | <1 | <1 |
| Sugars | 1-5 | 90-95 | 25-30 | <1 |

Table 2 shows the distribution of low molecular weight (monomers, dimers, etc.) versus higher molecular weight (>10 units) flavanol species in Fractions B and C as measured by thiolysis and gel permeation chromatography (Gu et al., J Agric Food Chem 50:4852-4860, 2002; Hammerstone et al., J Agric Food Chem 47:490-496, 1999). Fraction B contains more than 50% monomers, for example more than 60% or 70% monomers. In some examples Fraction B contains 70-80% monomers. Fraction B also contains more than 5% or 6% dimers, for example 5-7% dimers, such as 6.5% dimers. The high concentration of monomeric species in Fraction B is not expected owing to the high molecular weight filtration membrane (100-500 kD). Only flavanols with very low degrees of polymerization (dp) are absorbed in the small intestine (Del Rio et al., Antioxid Redox Signal 18:1818-1892, 2013) and thus Fraction B would be appropriate for systemic absorption to have physiologic effects such as enhancing endothelial function or other actions that require absorption of flavanols into the blood stream. This concentration of low molecular weight flavanol species (low mdp) is quite different from that of the whole grape seed that contains both high and low molecular weight flavanol species (Table 3). Moreover, Fraction B compares very favorably with commercially available grape seed extracts (Table 3). The higher molecular weight flavanol species comprising Fraction C can be metabolized by the colonic microflora along with the fiber in this fraction that is also readily fermented; Fraction C therefore is ideally suited to delivering prebiotic effects to the large colon.

TABLE 2

Flavanol composition of Fractions B and C (% of total flavanols)

| Flavanol unit | Fraction B | Fraction C |
|---|---|---|
| Monomer (n = 1) | 76.13 | 19.03 |
| Dimer (n = 2) | 6.55 | 1.63 |
| Trimer (n = 3) | 3.03 | 0.75 |
| Tetramer (n = 4) | 2.37 | 0.59 |
| Pentamer (n = 5) | 1.89 | 0.47 |
| Hexamer (n = 6) | 0.91 | 0.22 |
| Heptamer (n = 7) | 0.45 | 0.11 |
| Octamer (n = 8) | 0.12 | trace |
| Nonamer (n = 9) | trace | trace |
| Decamer (n = 10) | trace | trace |
| n > 10 | 8.55 | >60 |

Table 3 summarizes the phenolic attributes of whole dried Chardonnay grape seed, Fractions B and C with and without HPMC treatment and a variety of commercially available grape seed products. Analysis of mdp and total phenolic content was performed as described above. Fraction B has a very low mean dp value of 2.3 consistent with it being comprised mainly of monomeric and dimeric flavanols. Fraction B compares very well with other commercial grape seed extracts and in fact, the mean dp value of Fraction B is the lowest of all commercial samples tested. Thus, it is possible that existing industrial methods that attempt to maximize polyphenol extraction from grape seeds and further generate grape seed extracts standardized to high phenolic content (>70%) with adsorption methodology may sacrifice the ability to limit the size distribution of flavanols to less than 10 dp. The dp value of Fraction C is only slightly lower than those of whole Chardonnay seeds or commercial Chardonnay seed flour and reflects the fact that higher molecular weight flavanols comprise the majority of phenolic compounds in this fraction. Optional treatment with HPMC did not alter the mdp value of fraction B whereas it lowered the mdp value of Fraction C considerably. The HPMC treatment apparently removes a substantial amount of the high molecular weight flavanols and tannins comprising the Chardonnay seed. As shown in Table 3, Fractions B and C have considerably less lipid content compared to the other commercial grape seed extracts rendering them more amenable to tablet formulations. It is possible that the use of solvents in existing commercial extraction processes leads to increased extraction of lipid from the starting material; as shown in Table 3 grape seeds contain significant lipid fractions.

Although the Chardonnay seed itself has a high content of monomers, the lack of size selectivity of many prior processes is due to those methods attempting to maximize the extraction of all polyphenol/flavanol content from the seed using harsh conditions like high heat or solvents like ethanol. Not only do these conditions reduce selectivity of the dp of the extract, but the extract also has a substantial amount of larger procyanidins and tannins. The use of harsh and sometimes toxic solvents is also a disadvantage of those prior methods. The new extraction methods disclosed herein are carried out at less than the boiling point of water in aqueous solvents such as pure water that are substantially free of mineral acids and/or alcohols (such as ethanol), and do not require adsorbent resins or acidification of the extract. The process can also be carried out at atmospheric or ambient pressure, for example without pressurizing vessels to below or above atmospheric or ambient pressure for extraction. The presently disclosed examples of the filtration process provide a Chardonnay seed extract having less than 70% phenolics, for example less than 60% or 50% phenolics (such as polyphenols), but that selectively extract lower mdp fractions.

TABLE 3

Mean degree of polymerization (mdp), total phenolic content, and lipid content of grape seed products (dry basis)

| Sample | Mean dp (n) | % phenolics (GAE) | Lipid content (%) |
|---|---|---|---|
| Fraction B | 2.3 | 38.3 | 0.1-0.5 |
| Fraction C | 5.7 | 45.7 | 0.1-0.5 |
| Fraction B with HPMC treatment | 2.2 | 14.8 | 0.1-0.5 |
| Fraction C with HPMC treatment | 2.7 | 17.1 | 0.1-0.5 |
| Whole dried Chardonnay seeds (California source) | 6.8 | 14.0 | 20.08 |
| Whole dried Chardonnay seeds (Washington source) | 7.8 | 10.6 | 15.53 |
| Commercial defatted Chardonnay seed flour | 5.8 | 8.1 | 7.47 |
| Commercial grape seed extract 1 | 16.7 | >95 | 2.25 |
| Commercial grape seed extract 2 | 3.7 | >95 | 2.29 |
| Commercial grape seed extract 3 | 5.2 | >95 | 2.12 |
| Commercial grape seed extract 4 | 5.1 | >95 | 2.15 |
| Commercial grape seed extract 5 | 6.81 | >95 | 1.31 |

Example 3

Washing Step

This example illustrates a beneficial effect of seed washing on polyphenol yield prior to ultrafiltration. Although seed washing is shown to improve phenolic recovery at lower extraction temperatures, the washing step is not an essential component of the method disclosed in Example 1. The washing step instead confers an additional benefit on the separation method separately described in Example 1, and the washing step should therefore not be considered a requirement of the method.

Although the primary goal of the disclosed extraction process is aimed at separating different components of the grape seed for use in different applications, improved yield efficiencies (for both weight and polyphenols) are helpful to achieve better commercial viability. As described above, existing processes often include harsh solvents and/or high extraction temperatures to maximize extraction yields but these conditions are undesirable for a variety of reasons. In particular regard to the flavanol composition of grape seeds, high temperatures promote their polymerization. Accordingly, extraction at higher temperatures reduces the monomeric and dimeric content and increases the mean degree of polymerization of the resulting extracts.

To determine the relative efficiencies of the initial method steps (prior to step 5 in FIG. 1), Chardonnay grape seeds were subjected to identical extraction conditions as in Example 1, except for extraction temperature and the presence or absence of washing the seeds with room temperature water (step 1 in FIG. 1). As shown in Table 4, fresh whole unwashed Chardonnay seeds that were extracted at the higher temperature (180° F.) versus a lower temperature (130° F.) produced better extraction yield (12.81% versus 11.39%), phenolic recovery (91.07% versus 70.80%), and higher phenolic content of the resulting extract (51% versus 39.65%). Moreover, although drying the grape seeds prior to extraction at the lower temperature improved the extraction yield (to 12.49%) and phenolic content of the resulting extract (to 47.21%), phenolic recovery remained considerably lower (84.30%) compared to that obtained with the higher extraction temperature.

Surprisingly, extraction of washed fresh grape seeds at the lower temperature (130° F.) produced an essentially identical extraction yield, phenolic recovery and phenolic content of the extract to those produced by extraction at the higher temperature. Thus the addition of a washing step prior to extraction and ultrafiltration surprisingly increases extraction efficiencies without engendering the increased potential for flavanol polymerization as an artifact of increased extraction temperatures. The seed material removed by the washing procedure is quantitatively substantial (roughly 3.5% of the seed weight and surprisingly up to 50% of both the sugar and lipid content) and represents undesirable components of the grape seed (mainly sugars, lipids, and organic acids). Although not wishing to be bound by theory, it is possible that removal of these seed components by gentle washing facilitates phenolic recovery at lower temperatures.

TABLE 4

Extraction efficiencies at different temperatures and with and without washing

| Starting material | Extraction temperature (° F.) | Washing step | % phenolics of dry extract (GAE) | Phenolic recovery (% of total seed phenolic content) | Extraction yield (% dry seed weight) |
|---|---|---|---|---|---|
| Fresh whole Chardonnay seeds | 180 ± 5 | no | 51.00 | 91.07 | 12.81 |
| Fresh whole Chardonnay seeds | 130 ± 5 | no | 39.65 | 70.80 | 11.39 |
| Fresh whole Chardonnay seeds | 130 ± 5 | yes | 51.74 | 92.39 | 12.74 |
| Dry whole Chardonnay seeds | 130 ± 5 | no | 47.21 | 84.30 | 12.49 |

Example 4

Combination Compositions

The unexpected low mdp values of Fraction B suggest that Fraction B is well suited to impart beneficial effects on endothelial function and therefore support healthy circulation; based on the literature related to the effects of grape seed extract (Vislocky and Fernandez, Nutr Rev 68:656-670, 2010), the amount of Fraction B necessary to improve endothelial function ranges from 50 to 2000 mg. The critical role of the cardiovascular system in maintaining brain health is well known; the complex patterns of activity and structural change occurring at trillions of synapses create extraordinary metabolic demand. Indeed, while the brain accounts for only 2% of our body weight, it receives 20-25% of the body's blood flow, oxygen and circulating nutrients (Nichols et al., *From Neuron to Brain*, 2011; Kalaria, Nutr Rev 68:S74-S87, 2010). Lack of oxygen for even just a few minutes can result in injury and/or death of neurons and it is well known that long-term vascular insufficiency is associated with cognitive decline (Kalaria, Nutr Rev 68:S74-S87, 2010; Marshall and Lazar, Stroke 42:221-226, 2011). Thus, healthy circulation is critically important for maintaining optimal cognition on a moment-to-moment basis and moreover, the creation of new synapses requires the formation of new blood vessels (angiogenesis) for adequate provision of oxygen and nutrients. Hence, Fraction B could also be used as an ingredient in nutraceuticals designed to support or maintain cognitive health. For example, Fraction B could be combined with other natural ingredients demonstrated to affect various aspects of brain health and cognition as described below:

Guarana (*Paullinia cupana*), a plant of the maple family, is native to the central Amazon and has a long history of traditional use as tea made from the seeds. Multiple active ingredients are found in guarana including caffeine, theobromine, saponins, tannins, and catechin monomers (most notably catechin and epicatechin). Several double-blind, placebo-controlled, cross-over clinical studies in young healthy adults demonstrate that consumption of guarana extract (35-300 mg) improved memory, attention, cognitive speed, focus, alertness, mental acuity and mood over a period of at least six hours (Haskell et al., J Psychopharm 21:65-70, 2007; Kennedy et al., Pharmacol Biochem Behav 79:410-411, 2004; Kennedy et al., Appetite 50:506-513, 2008; Scholey et al., Nutrients 5:3589-3604, 2013). These effects were unlikely to be due to the caffeine content and indeed, higher doses of guarana extract, containing more caffeine were found to be less effective at improving cognitive performance (Haskell et al., J Psychopharm 21:65-70, 2007). Preclinical studies also provide evidence for improved memory performance and anxiety-reducing properties of guarana (Roncon et al., Planta Med 77:236-241, 2011; Espinola et al., J Ethnopharmacol 55:223-229, 1997).

The critical role of B vitamins in maintaining cognitive health is undisputed and B vitamin deficiencies are associated with and perhaps causal to several neurological deficits (Selhub et al., Nutr Rev 68:S112-S118, 2010). The B vitamins B6, B12, and folate are cofactors and/or substrates for enzymes involved in one-carbon metabolism which is critical for the synthesis of vital brain constituents such as neurotransmitters, phopholipids, and myelin. Recently these B vitamins were tested in a placebo-controlled trial in an elderly population with mild cognitive impairment (de Jager et al., Int J Geriatr Psychiatry DOI:10.1002/gps.2758; Smith et al., PLoS ONE 5(9): e12244. doi:10.1371/journal.pone.0012244, 2010) and shown to attenuate significantly the age-related reductions in both brain structure and cognitive function; over a period of two years, not only was brain volume shrinkage reduced by 30%, but executive cognition was stabilized as well. At baseline, the entire study population included subjects with normal levels of circulating homocysteine. Larger benefits were observed, however, in those subjects with elevated plasma levels of homocysteine at baseline. Vitamins B6, B12 and folic acid would be beneficial in doses ranging from their respective RDAs to the 10% below their respective Upper Limits (Bowman et al., Neurology 78:241-249, 2012). In some examples, vitamin B6 could be present in a dose of 1.5-90 mg (such as 10, 20 or 30 mg), vitamin B12 in a dose of 2.4-1000 mcg (such as 400, 550, 700 or 800 mcg), and folate or folic acid present in a dose of 400-900 mcg (such as 550, 700, or 800 mcg).

Blueberries contain epicatechin, chlorogenic acid and pterostilbene; these polyphenols are bioavailable and laboratory studies have demonstrated that epicatechin and pterostilbene cross the blood-brain barrier (Williams and Spencer, Free Radic Biol Med 52:35-45, 2012; Joseph et al., J Agric Food Chem 56:10544-10551, 2008). In laboratory studies, blueberry extract stimulated the production of neuronal growth factors and biochemical signals involved in the formation of new neurons, increased the number of neurons in the hippocampus (Casadesus et al., Nutr Neurosci 7:309-316, 2004), and increased the levels of biochemical signals used for communication between neurons (Williams et al., Free Rad Biol Med 45:295-305, 2008). Based on these studies, blueberry powder or blueberry extract would be beneficial at doses ranging from 10 mg-1 gram.

Green coffee bean extract contains bioavailable chlorogenic acids (Farah et al., J Nutr. 138:2309-2315, 2008) which have been shown in laboratory studies to stimulate growth and development of neurons, inhibit the activity of enzymes that degrade neurotransmitters and protect neurons against oxidative stress (Ito et al., Biosci Biotechnol Biochem 72:885-888, 2008; Kwon et al., Eur J Pharmacol 649:210-217, 2010). From these studies, green coffee bean extract would be beneficial in doses of 15 mg-500 mg.

The products produced by the newly disclosed extraction processes may be used in foods, beverages and nutraceuticals as an antioxidant and to promote cardiovascular and cognitive health. The antioxidant properties of the extracts are beneficial across a wide range of applications. Thus, foods, beverages, dietary supplements, nutraceutical products and cosmetics containing the polyphenolic products of the presently disclosed processes may be produced. The Chardonnay grape seed extract, in liquid or powder form, may be used as a colorant in food products, beverages, cosmetics and dietary supplements.

In certain examples, the concentration of any of the natural products, nutrients, or additives in the composition is in the range of zero to ten percent, for example in the range of 0.04 to 45 percent, such as in the range of 5 to 25 percent.

Examples of compositions such as unit dosage forms containing sufficient amounts of Chardonnay seed extract (Fraction B), guarana extract, vitamin B6, vitamin B12, folate, blueberry powder/extract and green coffee bean extract would be useful for promoting cognitive and brain health.

Example 5

Compositions, Formulations and Packaging

The grape seed extracts and compositions can be formulated in pharmaceutically acceptable carriers, for example to produce nutraceuticals in the form of dietary supplement dosage forms (such as tablets or capsules), liquids (such as beverages or gels), and consumable products (such as foods or powders that are mixed with liquids). Formulations for such compositions are well known in the art. For example, Remington's Pharmaceutical Sciences, by E. W. Martin, Mack Publishing Co., Easton, Pa., 19th Edition, 1995, describes exemplary formulations (and components thereof) suitable for delivery of the disclosed compositions. In some examples, the compositions also include additional agents such as guarana extract, vitamin B6, vitamin B12, folate, blueberry powder/extract and green coffee bean extract. Compositions comprising at least one of these compounds can be formulated for use in human or veterinary medicine. Particular formulations of a disclosed pharmaceutical composition may depend, for example, on the mode of administration (e.g., oral, topical or parenteral) and/or on the condition to be treated. In some embodiments, formulations include a pharmaceutically acceptable carrier in addition to at least one active ingredient.

Parenteral formulations usually comprise injectable fluids that include pharmaceutically and physiologically acceptable fluids such as water, physiological saline, balanced salt solutions, aqueous dextrose, glycerol or the like as a vehicle. For solid compositions such as powder, pill, tablet, or capsule forms conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances or excipients, such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin.

The composition is optionally used in a number of forms. For example, the composition can be a solution that is ready to drink from a small container, in a dilute form from a larger container, or as a teaspoon dose. However, the composition can in some examples be provided as a concentrate, allowing the user to mix with water or into a food or beverage. Alternatively it can be provided in the form of a sublingual spray, or in powder form that is mixed by the user as needed into a solution, is added directly to a food substrate, or is directly ingested. In another example, the composition is contained in a gauze bag, suitable for brewing like that of a tea bag and/or coffee pod. Alternatively, the formulation is contained as a dry powder in a pouch, such as an easy tear open flexible mini-pouch containing one or more servings.

Packaging for the formulation can be any package or container for holding a solid, liquid, emulsion, suspension, or the like, such as a can, a bottle, a pouch, gauze bag, or a packet. The packaging is optionally for bulk product, multiple servings, or single dose. In another example the composition is provided in liquid form in a bottle, such as a spray bottle, for example a sublingual spray delivery bottle, or in a bottle with a dropper tapered at one end. Yet another embodiment includes any combination and/or permutation of any of the nutritional constituents described herein.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A composition comprising an effective amount of a water extract of Chardonnay grape seed and a pharmaceutically acceptable carrier, wherein the extract consists essentially of Fraction B or C which comprise by percentage dry weight:
    Fraction B:
        38-50% Polyphenols,
        9-12% Fiber,
        1-2% Protein,
        <1% Lipids,
        25-30% Sugars; and
    Fraction C:
        45-55% Polyphenols,
        26-30% Fiber,
        2-3% Proteins,
        <1% Lipids,
        <1% Sugars;
    wherein the extract is obtained by the steps of:
    (a) mixing washed grape seeds with heated water at a temperature below 100° C.

2. The composition of claim 1, wherein the water extract consists essentially of Fraction C, and wherein the flavanols in Fraction C have a mean degree of polymerization of 5-6.

3. The composition of claim 2, wherein the water extract consists essentially of Fraction B wherein the flavanols in Fraction B have a mean degree of polymerization of less than 3 and are more than 50% monomers.

4. The composition of claim 1, having less than 50% polyphenols.

5. The composition of claim 1, wherein the water extract has undergone sequential ultrafiltrations.

6. The composition of claim 5, wherein the water extract contains flavanols having a mean degree of polymerization (mdp) of less than 3.

7. The composition of claim 6, wherein the composition has an mdp of less than 2.5.

8. A tablet composition comprising the composition of claim 1, and further comprising a nutrient.

9. The corn position of claim 1, wherein the water extract consists essentially of Fraction B, and wherein Fraction B is further obtained by the step of concentrating and drying the second permeate.

10. The composition of claim 1, wherein the water extract consists essentially of Fraction C, and wherein Fraction C is further obtained by the step of concentrating and drying the second retentate.

11. The composition of claim 1, wherein the water extract is the second permeate, wherein less than 10% of the polyphenols in the water extract contain more than 10 monomeric units, and the second permeate has a mdp of less than 2.5.

12. The composition of claim 1, wherein the water extract is the second retentate and the polyphenols in the second retentate have a mdp of greater than 5.

13. The composition of claim 1, wherein said composition is formulated as a dietary supplement or food product.

14. The composition of claim 13, wherein the water extract consists essentially of Fraction B, and wherein the composition further comprises guarana extract, vitamin B6, vitamin B12, folate, blueberry powder/extract and green coffee bean extract.

15. The composition of claim 1, wherein the water extract consists of Fraction B.

16. A pharmaceutical tablet formulation comprising an effective amount of a water extract of Chardonnay grape seed and a pharmaceutically acceptable carrier, wherein the extract consists essentially of Fraction B or C which comprise by percentage dry weight:

Fraction B:
   38-50% Polyphenols,
   9-12% Fiber,
   1-2% Protein,
   <1% Lipids,
   25-30% Sugars; and
Fraction C:
   45-55% Polyphenols,
   26-30% Fiber,
   2-3% Proteins,
   <1% Lipids,
   <1% Sugars.

17. The tablet formulation of claim 16, comprising Fraction B.

18. The tablet formulation of claim 16, comprising Fraction C.

\* \* \* \* \*

UNITED STATES PATENT AND TRADEMARK OFFICE
CERTIFICATE OF CORRECTION

PATENT NO. : 10,709,751 B2
APPLICATION NO. : 16/022422
DATED : July 14, 2020
INVENTOR(S) : Ianiro et al.

Page 1 of 1

It is certified that error appears in the above-identified patent and that said Letters Patent is hereby corrected as shown below:

In the Claims

Column 22, Line 38, in Claim 9 "The corn position of claim 1, wherein the water extract," should read --The composition of claim 1, wherein the water extract--.

Signed and Sealed this
Twenty-ninth Day of September, 2020

Andrei Iancu
*Director of the United States Patent and Trademark Office*